(12) United States Patent
Kasagi et al.

(10) Patent No.: US 8,524,864 B2
(45) Date of Patent: Sep. 3, 2013

(54) METHOD FOR PRODUCING CONJUGATE OF THYROXINE AND ALBUMIN

(75) Inventors: Noriyuki Kasagi, Kanagawa (JP); Tadahiro Matsuno, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/213,585

(22) Filed: Aug. 19, 2011

(65) Prior Publication Data

US 2012/0046447 A1 Feb. 23, 2012

(30) Foreign Application Priority Data

Aug. 20, 2010 (JP) ................................ 2010-184649

(51) Int. Cl.
*C07K 1/107* (2006.01)
*C07K 14/76* (2006.01)

(52) U.S. Cl.
USPC ...................................... 530/362; 424/195.11

(58) Field of Classification Search
USPC ..................................... 530/362; 424/195.11
See application file for complete search history.

(56) References Cited

U.S. PATENT DOCUMENTS 4,040,907 A 8/1977 Ullman et al.
5,834,206 A 11/1998 Neuenhofer et al.

FOREIGN PATENT DOCUMENTS

JP 8-233812 A 9/1996

OTHER PUBLICATIONS

BSA-Thyroxine conjugate < http://www.abdserotec.com/product/thyroxine-purified-protein-8960-1204.html > downloaded Sep. 13, 2012.*
C. W. Burke et al.: Rapid Purification of Tri-Iodothyronine and Thyroxine Protain Conjugates for Antibody Production; Journal of Endocrinology: vol. 65; No. 1; 1975; pp. 133-138.
Extended European Search Report dated Jan. 24, 2012 issued in corresponding European patent application No. 11178083.9.
V. Kruse: Production and Evaluation of High-Quality Thyroxine Antisera for Use in Radioimmunoassay; Scandinavian Journal of Clinical & Laboratory Investigation; vol. 36; No. 1; Jan. 1, 1976; pp. 95-101.

* cited by examiner

*Primary Examiner* — Chih-Min Kam
(74) *Attorney, Agent, or Firm* — Birch, Stewart, Kolasch & Birch, LLP

(57) ABSTRACT

It is an object of the present invention to provide a method for producing a conjugate of thyroxine and albumin with higher purity. The present invention provides a method for producing a conjugate of thyroxine and albumin which comprises: step (a) of converting a carboxyl group in thyroxine having a carboxyl group to be linked to albumin into an active ester and allowing the thyroxine to react with albumin, so as to prepare a conjugate of thyroxine and albumin; and step (b) of purifying the conjugate with the use of an acidic mixed aqueous solvent in which the thyroxine having a carboxyl group to be linked to albumin is dissolved but albumin is not precipitated.

6 Claims, 2 Drawing Sheets

METHOD FOR PRODUCING CONJUGATE OF THYROXINE AND ALBUMIN

TECHNICAL FIELD

The present invention relates to a method for producing a conjugate of thyroxine and albumin.

BACKGROUND ART

Thyroxine (T4) is a type of thyroid hormone secreted from the thyroid, and it is represented by the structural formula shown below. In general, thyroxine (T4) affects cells throughout the body and accelerates the cellular turnover rate. In addition to thyroxine, triiodothyronine (T3) is known as a thyroid hormone, and thyroxine (T4) accounts for a major share of the thyroid hormones circulating in the blood.

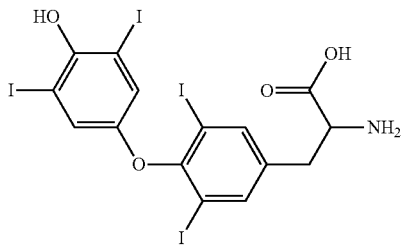

T4

A conjugate of thyroxine and bovine serum albumin (BSA) (hereafter referred to as "T4-BSA") is used as a polyhapten or the like for preparing an anti-thyroxine antibody. In addition, T4-BSA is utilized in competitive assays of T4 and the like. The present inventors have attained results of competitive assays of T4 and the like indicating that the performance of T4-BSA depends on the degree of purity of T4-BSA instead of the labeling index of T4 for BSA. Since T4-BSA production involves the use of excess T4 derivatives, unreacted T4 derivatives cannot be completely removed via conventional techniques such as dialysis or gel filtration conducted with the use of an aqueous solvent.

A hapten tracer complex comprising a hapten linked directly or via a spacer group to an indicator component and an antibody capable of specifically linking to the indicator component has been known (see JP Patent Publication (Kokai) No. H08-233812 A (1996)) in connection with a technique for eliminating adverse results of analysis caused by unstability and non-specific linkage of a hapten tracer in immunoassay in which hapten is linked to an indicator component. According to the method for producing such complex, an antibody against an indicator component is mixed with hapten linked to an indicator component in an aqueous solution, and an organic solvent (e.g., acetonitrile) is added to the aqueous solution in order to improve the solubility of hapten linked to an indicator component.

However, no technique involving the use of an organic solvent such as acetonitrile for purification of T4-BSA has been known to date.

SUMMARY OF THE INVENTION

It is an object of the present invention to provide a method for producing a conjugate of thyroxine and albumin with higher purity.

The present inventors have conducted concentrated studies in order to attain the above object. As a result, they discovered that unreacted thyroxine derivatives could be more efficiently removed via purification of the conjugate of thyroxine and albumin with the use of a mixed aqueous solvent having a given degree of acidity. The present invention has been completed based on such finding.

The present invention provides a method for producing a conjugate of thyroxine and albumin which comprises:
step (a) of converting a carboxyl group in thyroxine having a carboxyl group to be linked to albumin into an active ester and allowing the thyroxine to react with albumin, so as to prepare a conjugate of thyroxine and albumin; and
step (b) of purifying the conjugate with the use of an acidic mixed aqueous solvent in which the thyroxine having a carboxyl group to be linked to albumin is dissolved but albumin is not precipitated.

Preferably, in step (b), the conjugate is purified by eluting unreacted thyroxine having a carboxyl group to be linked to albumin in the mixed aqueous solvent.

Preferably, in step (b), the conjugate is purified by dialyzing the reaction product obtained in step (a) in the mixed aqueous solvent.

Preferably, in step (b), the conjugate is purified via gel filtration.

Preferably, the mixed aqueous solvent is a mixture of water, acetonitrile, and trifluoroacetic acid.

Preferably, step (a) is carried out under neutral or basic conditions.

The present invention further provides a conjugate of thyroxine and albumin which is obtained by the aforementioned method of the present invention.

According to the production method of the present invention, a conjugate of thyroxine and albumin with higher purity can be produced. The conjugate produced by the method of the present invention is capable of yielding higher signal sensitivity in applications such as ELISA or competitive assays.

EMBODIMENTS OF THE INVENTION

Figure 1:
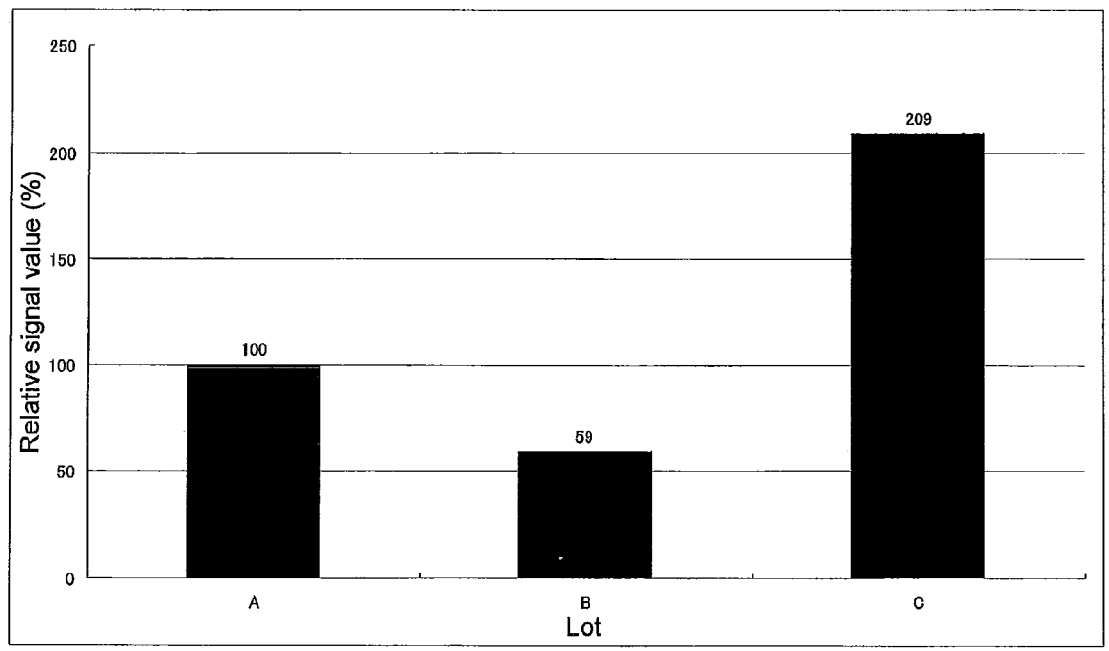
FIG. 1 shows the results of evaluation by the fluorescent particle method conducted in the examples.

The production method of the present invention comprises: step (a) of converting a carboxyl group in thyroxine having a carboxyl group to be linked to albumin into an active ester and allowing the thyroxine to react with albumin, so as to prepare a conjugate of thyroxine and albumin; and step (b) of purifying the conjugate with the use of an acidic mixed aqueous solvent in which the thyroxine having a carboxyl group to be linked to albumin is dissolved but albumin is not precipitated.

The condition in which "albumin is not precipitated" in the acidic mixed aqueous solvent of the present invention is a condition in which "albumin is dissolved or suspended" therein.

In the present invention, the constitution of thyroxine having a carboxyl group to be linked to albumin (hereafter occasionally referred to as a "thyroxine derivative") that can be used for preparing the conjugate of thyroxine and albumin is not particularly limited, provided that such thyroxine is capable of forming a conjugate with albumin. Thyroxines having various modifications are within the scope thereof. For example, a derivative resulting from introduction of a linker having a carboxyl group at the terminus into an amino group of thyroxine having a carboxyl group that has been esterified in advance can be used. A linker portion may be composed of a combination of groups selected from, for example, —O—, —NH—, —CO—, and lower alkylene groups. The carboxyl terminus of such thyroxine derivative may be converted into an active ester and may be bound to the amino group of albumin. Thus, a conjugate of thyroxine and albumin can be produced. Active esterification of a carboxyl group of the thyroxine derivative can be realized with the use of, for example, 1-ethyl-3-(3-dimethylaminopropyl)carbodiimide hydrochloride (WSC), N-hydroxysuccinimide (NHS), or N-hydroxysulfosuccinimide (sulfo-NHS).

The term "conjugate of thyroxine and albumin" used herein preferably refers to a conjugate composed of thyroxine covalently bound to albumin.

Specifically, the thyroxine having a carboxyl group to be linked to albumin in the present invention is preferably represented by the following formula (1):

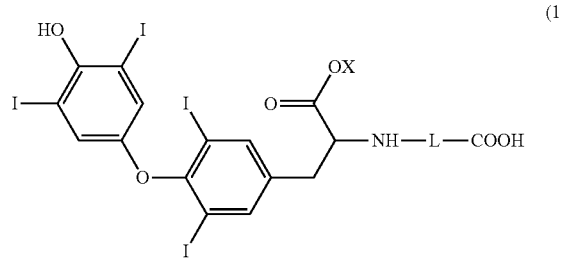

(1)

wherein X represents a lower alkyl group and preferably a methyl or ethyl group; and L represents a linker.

A linker represented by L is preferably composed of a combination of groups selected from, for example, —O—, —NH—, —CO—, and lower alkylene (preferably $C_{1-4}$ alkylene) groups.

The conjugate of thyroxine and albumin of the present invention can be produced by converting a carboxyl group in the compound represented by the formula (1) into an active ester, following which such compound is allowed to react with albumin.

Examples of albumins used in the present invention include egg albumin, serum albumin, and lactalbumin. Serum albumin is preferably used, bovine serum albumin (BSA), human serum albumin, guinea pig serum albumin, mouse serum albumin, porcine serum albumin, rabbit serum albumin, rat serum albumin, sheep serum albumin, and the like are commercially available, and use of bovine serum albumin (BSA) is more preferable.

In the present invention, the conjugate of thyroxine and albumin can be produced without particular limitation. For example, a carboxyl group of the thyroxine derivative is converted into an active ester, excess amounts of such thyroxine derivative and albumin are dissolved in phosphate buffer, and the resulting solution is incubated for a given period of time. The step of producing the conjugate of thyroxine and albumin is preferably carried out under neutral or basic conditions. The pH level of a reaction solution is, for example, 6.5 to 11, preferably 6.5 to 9, more preferably 6.5 to 7.5, and most preferably 7.0. The resulting reaction solution can be roughly purified via centrifugation, filtration or other means prior to the step of purification of the present invention.

The present invention comprises purifying the conjugate of thyroxine and albumin which was obtained from the above-obtained reaction product containing such conjugate with the use of an acidic mixed aqueous solvent in which the thyroxine derivative is dissolved but albumin is not precipitated. Since the reaction product contains large amounts of unreacted thyroxine derivatives, such unreacted thyroxine derivatives are removed more efficiently by the process of purification of the present invention. In addition, a thyroxine derivative that is hydrophobically bound to albumin can be efficiently removed.

The acidic mixed aqueous solvent used in the present invention is substantially composed of water, acid, and a given organic solvent. Examples of acids include trifluoroacetic acid, hydrochloric acid, sulfuric acid, acetic acid, and trichloroacetic acid, and the use of trifluoroacetic acid is preferable. Examples of organic solvents include acetonitrile, N,N-dimethylformamide (DMF), dimethyl sulfoxide (DMSO), and methanol, and the use of acetonitrile is preferable.

The mixing ratios for water, acid, and organic solvents are not particularly limited, provided that the thyroxine derivative is dissolved but albumin is not precipitated in an acidic mixed aqueous solvent. For example, the ratio of water to an organic solvent is 30:70 to 70:30, preferably 35:65 to 65:30, more preferably 40:60 to 60:40, and particularly preferably 45:55 to 55:45. Acid concentration in the mixed aqueous solvent can be, for example, 0.001% to 5% by weight and preferably 0.01% to 2% by weight. The degree of acidity (pH) of the mixed aqueous solvent of the present invention is preferably 0 to 6, more preferably 0 to 4, and most preferably 1 to 3, when it is measured with the use of a pH test paper. Acidification of the mixed aqueous solvent causes gradual changes in albumin conformations, and the thyroxine derivative included in albumin is eluted in the mixed aqueous solvent. While the thyroxine derivative containing a phenolic hydroxyl group or a carboxyl group is less likely to dissolve in water under acidic conditions, elution of the thyroxine derivative can be ensured with the use of the acidic mixed aqueous solvent.

When the conjugate is purified with the use of the thus-obtained acidic mixed aqueous solvent, unreacted thyroxine derivatives can be separated in the mixed aqueous solvent in a more efficient manner, and the conjugate of the present invention with higher purity can be obtained. Specifically, the conjugate of the present invention can be separated from unreacted thyroxine derivatives via dialysis, gel filtration, or other means with the use of an acidic mixed aqueous solvent. When separation is carried out via dialysis, the reaction product of the thyroxine derivative and albumin is added to an adequate dialysis membrane, the dialysis membrane is introduced into the acidic mixed aqueous solvent of the present invention, and the solvent in the reaction product in the dialysis membrane is substituted with an acidic mixed aqueous solvent. Thus, unreacted thyroxine derivatives are eluted from the dialysis membrane and flow into the acidic mixed aqueous solvent outside the dialysis membrane. The molecular weight cut off of the dialysis membrane used in the present invention is not particularly limited, provided that the conjugate of the present invention can be separated from unreacted thyroxine derivatives. For example, a dialysis membrane with a molecular weight cut off of approximately 10,000 can be used. When separation is carried out via gel filtration, a column is filled with an adequate gel filtration carrier, the content of the column is substituted with the acidic mixed aqueous solvent of the present invention, the reaction product of the thyroxine derivative and albumin is introduced into a gel filtration column, and the acidic mixed aqueous solvent of the present invention is further introduced into the gel filtration column. Thus, the conjugate of the present invention can be separated from unreacted thyroxine derivatives. A specific example of a gel filtration carrier that can be used in the present invention is the Sephadex LH-20 (GE) having organic solvent tolerance. The amount of the mixed aqueous solvent used in the process of purification of the present invention is preferably 500 ml to 50 liters, more preferably 1 liter to 30 liters, and most preferably 2 liters to 15 liters, per 500 mg of BSA used as a starting material.

Hereafter, the present invention is described in greater detail with reference to the examples, although the present invention is not limited to the examples.

EXAMPLES

<Production of a Conjugate of Thyroxine and Bovine Serum Albumin>

Hereafter, T4 derivative 2 was synthesized from T4 derivative 1 in accordance with scheme 1.

Scheme 1

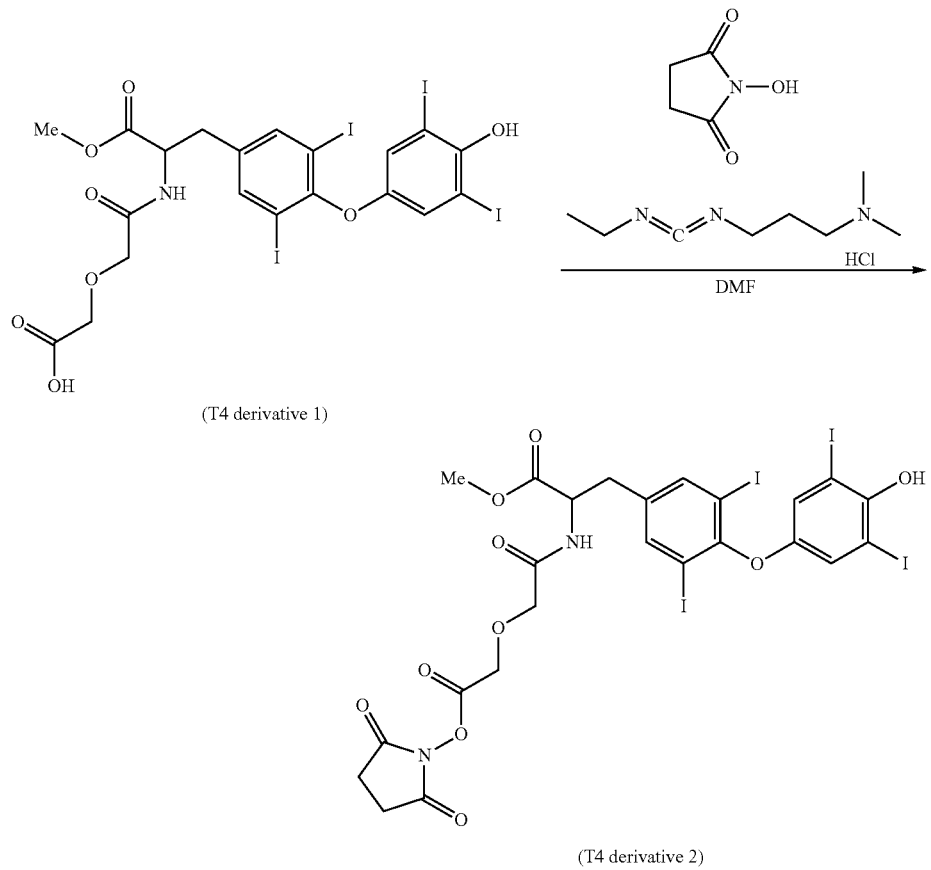

(T4 derivative 1)

(T4 derivative 2)

T4 derivative 1 (270 mg; method for synthesizing: same as that described in U.S. Pat. No. 4,040,907) was dissolved in dimethylformamide (DMF), and the solution was stirred at room temperature. Thereafter, 285 mg of 1-ethyl-3-(3-dimethylaminopropyl)carbodiimide hydrochloride (WSC, Dojindo Laboratories) and 174 mg of N-hydroxysuccinimide (NHS, Wako Pure Chemical Industries, Ltd.) were added thereto, and the mixture was stirred at room temperature for 2 hours to synthesize T4 derivative 2.

Subsequently, a conjugate of the resulting T4 derivative 2 and bovine serum albumin (BSA) (i.e., T4-BSA) was produced in accordance with scheme 2.

Scheme 2

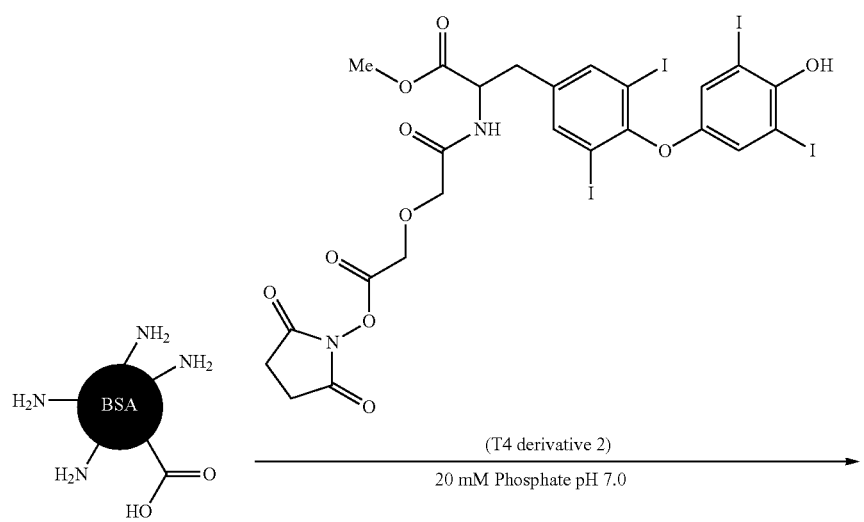

-continued

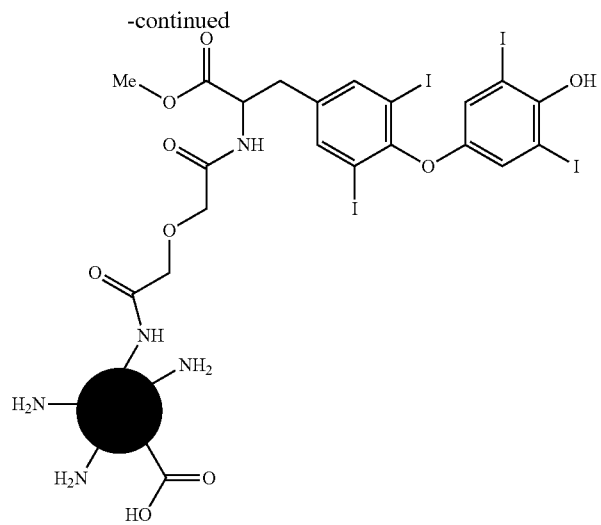

BSA (500 mg) was dissolved in 100 ml of 20 mM phosphate buffer (pH 7.0), and a DMF solution containing the T4 derivative 2 obtained above was added to the buffer. Thereafter, the mixture was allowed to stand at room temperature overnight.

After the completion of the reaction, a white precipitate was removed via centrifugation at 3,300 g at 4° C. for 30 minutes, and a supernatant was recovered. The recovered supernatant was filtered through a 0.22-μm filter, and the filtrate was purified via dialysis in the manner described below.

<Purification Via Dialysis>

The obtained filtrate was introduced into dialysis filter tube (product name: SnakeSkin Pleated Dialysis Tubing; MWCO: 10,000; dry diameter: 22 mm×35 ft; product number: 68100; Thermo Scientific). A mixed (1:1) solvent (5 liters) of ion exchange water ($H_2O$) and acetonitrile (AR) which contains 0.1% trifluoroacetic acid (TFA) was introduced into a 5 L beaker. The pH level of the mixed solvent was measured with the use of a pH test paper reel (Catalog number: Product code: KN3138095; Tech-Jam) and found to be 1. The dialysis filter tube containing the filtrate was introduced into the mixed solvent and slowly stirred at room temperature.

After dialysis, the aqueous solution in the dialysis tube was recovered. The recovered aqueous solution was poured into a 500-ml eggplant-shaped flask, frozen in liquid nitrogen, and then lyophilized. Thus, approximately 400 mg of a white solid was obtained as the conjugate of T4 and albumin of the present invention.

<Analysis of T4/BSA Value>

The number of T4 molecules bound to one molecule of BSA was measured as the T4/BSA value.

Measurement was carried out via MALDI-TOF-MS. Sinapic acid (Sigma-Aldridge) was used as a matrix. Sinapic acid was dissolved at 10 mg/ml in a mixed solution of water and acetonitrile (1:1) which contains 0.1% TFA so as to prepare a matrix solution. The matrix solution (5 μl) was mixed with the same amount of the aqueous T4-BSA solution (purified water), and the resulting mixture was thoroughly agitated by pipetting in a microtube. Thereafter, 5 μl of the mixture was added dropwise to an MS substrate plate, air-dried at room temperature, and then subjected to MS assay. Assay was carried out in the linear, positive mode for a molecular weight range of 60,000 to 100,000.

<Quantification of Amount of the Remaining T4>

The amount of unreacted T4 derivatives remaining in the T4-BSA sample obtained above (the lyophilized product) was determined via high-performance liquid chromatography in the manner described below. Hereafter, the measured value indicates the amount of the remaining T4 (wt %).

At the outset, approximately 7 mg of the lyophilized product obtained above was sampled, dissolved in 5 ml of a mixed solvent of acetonitrile and water (1:1), filtered through a 0.45-μm filter, and then injected into a column.

Measurement conditions are as described below.

(Measurement Conditions)
Column: TSKgel ODS-100Z (4.6×250 mm; lot number: P0103; Tosoh)
Guard column: C18; Waters
Eluant A: $H_2O$=100 (0.1% TFA)
Eluant B: acetonitrile=100 (0.1% TFA)
* Due to the volatility of TFA, eluants were prepared at the time of use.
Rinsing solution: acetonitrile:$H_2O$=9:1 vol.
Time course:

TABLE 1

| Time (min) | B. Pump (%) |
|---|---|
| 0.1 | 50 |
| 30 | 50 |
| 30.1 | 100 |
| 45 | 100 |
| 45.1 | 50 |
| 60 | Stopped |

Flow rate: 1.0 ml/min
Column temperature: 40° C.
Wavelength: 254 nm for Detector A
Sensitivity: AUX 2
Amount of injection: 10 μl
Sample concentration: 10 mg of T4-BSA (lyophilized product) was dissolved in a mixed solvent of AR:$H_2O$ (1:1).

<Evaluation by the Fluorescent Particle Method>

(Plate Preparation)
With the use of 150 mM NaCl, the concentration of the purified sample obtained above (the lyophilized product) was adjusted to 50 μg/ml. The solution (100 μl) was added to each well of a 96-well plate, and the 96-well plate was shaken at room temperature at 700 rpm for 1 hour. After the reaction, the supernatant was discarded, 350 μl of a blocking reagent (N102, NOF Corporation) was added, and the 96-well plate was shaken at room temperature at 700 rpm for 1 hour. After the completion of the reaction, the supernatant was discarded, 350 μl of Immunoassay Stabilizer (ABI) was added, and the 96-well plate was shaken at room temperature at 700 rpm for 0.5 hours. Thereafter, the supernatant was discarded and the plate was dried.

(Evaluation by Fluorometry)

The concentration of T4-antibody-labeled fluorescent particles (1% solid) (1% BSA; aqueous 1×PBS solution) were diluted to 0.0025% with the use of 1×PBS. The resulting dispersion was added to the 96-well plate at 100 μl/well, and the 96-well plate was shaken at room temperature at 700 rpm for 1 hour. After the completion of the reaction, the supernatant was discarded, the plate was washed four times with 300 μl of PBST, and assay was carried out with the use of a fluorescence plate reader (Ex=660 nm; Em=680 nm). The term "T4-antibody-labeled fluorescent particles (1% solid)" refers to a condition in which the solid concentration of the latex particle is 1 wt % (1 wt %=1 g of latex particles per 100 ml of water).

Comparative Examples

A conjugate was prepared in the same manner as in the examples above, except that a solvent used in the "purification conditions" column of Table 2 was used at the time of purification via dialysis. The produced conjugate was subjected to various analytical techniques and evaluated in the same manner as in the examples.

[Results]

Figure 2:
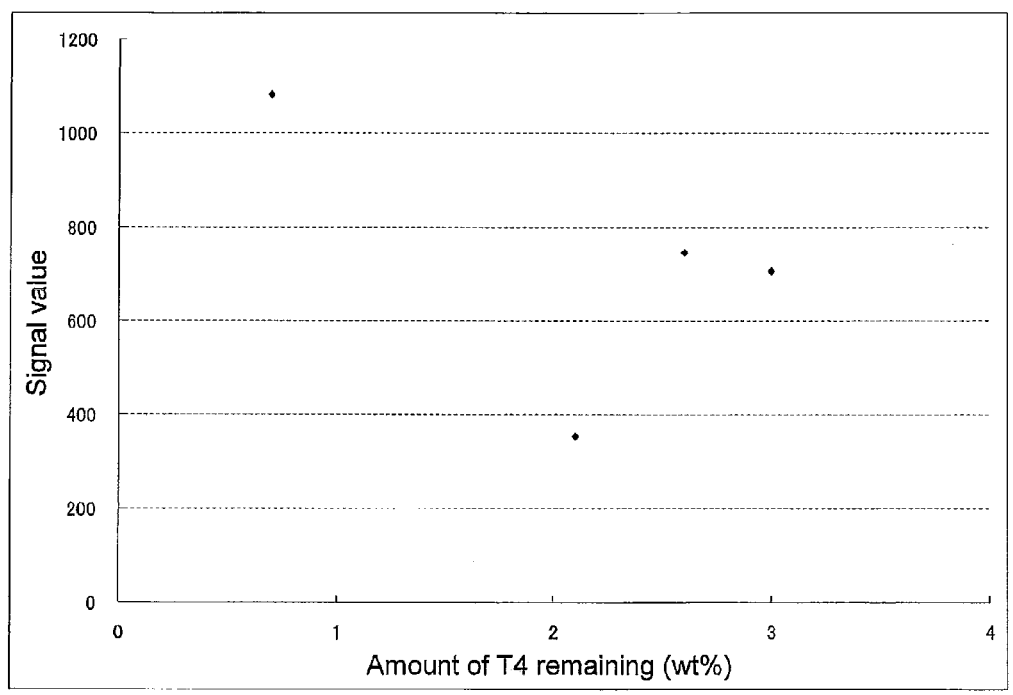
FIG. 2 shows the results of evaluation by the fluorescent particle method conducted in the examples.

Tables 2 and 3 below show the results of various forms of analysis of the conjugate of each lot produced in the examples and in the comparative examples. FIG. 1 shows the results of evaluation of the lots shown in Table 2 by the fluorescent particle method. In Table 2, a relative signal value (%) from the fluorescent particle method is a relative value determined based on the value of lot A, which was designated as 100%. FIG. 2 shows the correlation between the amount of the remaining T4 (wt %) and the average signal value determined by the fluorescent particle method for the lots shown in Table 3.

TABLE 2

| Lot | T4/BSA value | Amount of remaining T4(wt %) | Purification conditions | fluorescent particle method Relative signal value (%) |
|---|---|---|---|---|
| Comparative Example 1 | A | 8 | 5 | $H_2O$ | 100 |
| Comparative Example 2 | B | 6 | 3.7 | $H_2O$ | 59 |
| Example 1 | C | 6 | 0 | $H_2O$/AR = 1/1, 0.1% TFA | 209 |

AR: acetonitrile; TFA: trifluoroacetic acid

TABLE 3

| Lot | T4/BSA value | Amount of remaining T4(wt %) | Purification conditions | fluorescent particle method Average signal value (a.u.) |
|---|---|---|---|---|
| Comparative Example 3 | D | 6 | 3 | $H_2O$ | 707 |
| Comparative Example 4 | E | 6 | 2.1 | $H_2O$, 0.1% TFA | 354 |
| Comparative Example 5 | F | 6 | 2.6 | $H_2O$/AR = 1/1 | 747 |
| Example 2 | G | 6 | 0.7 | $H_2O$/AR = 1/1, 0.1% TFA | 1083 |

AR: acetonitrile; TFA: trifluoroacetic acid

The results of various analyses demonstrated that the amounts of the remaining T4 of the lots of the examples were lower than those of the comparative examples. In addition, the signal values of the lots of the examples determined by the fluorescent particle method were higher, regardless of T4/BSA value. Larger quantities of unreacted T4 derivatives remained in the lots of the comparative examples, and the relative signal values determined by the fluorescent particle method were lower than those of the examples.

The invention claimed is:

1. A method for producing a conjugate of thyroxine and albumin which comprises:
    step (a) of converting a carboxyl group in thyroxine having a carboxyl group to be linked to albumin into an active ester and allowing the thyroxine to react with albumin, so as to prepare a conjugate of thyroxine and albumin; and
    step (b) of purifying the conjugate with the use of an acidic mixed aqueous solvent in which the thyroxine having a carboxyl group to be linked to albumin is dissolved but albumin is not precipitated,
    wherein the thyroxine having a carboxyl group to be linked to albumin is represented by the following formula (1):

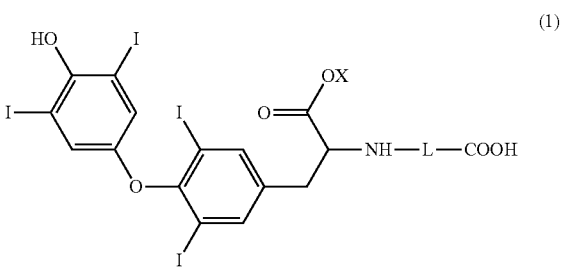

wherein X represents a lower alkyl group, and L represents a linker; and the acidic mixed aqueous solvent is composed of water, an acid and an organic solvent where the acid is selected from the group consisting of trifluoroacetic acid, hydrochloric acid, sulfuric acid, acetic acid and trichloroacetic acid, and the organic solvent is selected from the group consisting of acetonitrile, N,N-dimethylformamide, dimethyl sulfoxide and methanol.

2. The method according to claim 1, wherein, in step (b), the conjugate is purified by eluting unreacted thyroxine having a carboxyl group to be linked to albumin in the acidic mixed aqueous solvent.

3. The method according to claim 1, wherein, in step (b), the conjugate is purified by dialyzing the reaction product obtained in step (a) in the acidic mixed aqueous solvent.

4. The method according to claim 1, wherein, in step (b), the conjugate is purified via gel filtration.

5. The method according to claim 1, wherein the acidic mixed aqueous solvent is a mixture of water, acetonitrile, and trifluoroacetic acid.

6. The method according to claim 1, wherein step (a) is carried out under neutral or basic conditions.

* * * * *